(12) United States Patent
Staudinger et al.

(10) Patent No.: US 10,912,696 B2
(45) Date of Patent: Feb. 9, 2021

(54) DEVICE FOR LINEARLY MOVING A PATIENT SUPPORT SURFACE USING A HYDRAULIC CYLINDER AND A GEAR ARRANGEMENT

(71) Applicant: MAQUET GMBH, Rastatt (DE)

(72) Inventors: Martin Staudinger, Ettlingen (DE); Guido Koch, Karlsruhe (DE)

(73) Assignee: MAQUET GMBH, Rastatt (DE)

( * ) Notice: Subject to any disclaimer, the term of this patent is extended or adjusted under 35 U.S.C. 154(b) by 674 days.

(21) Appl. No.: 15/167,642

(22) Filed: May 27, 2016

(65) Prior Publication Data
US 2016/0270994 A1 Sep. 22, 2016

Related U.S. Application Data

(63) Continuation-in-part of application No. PCT/EP2015/050659, filed on Jan. 15, 2015.

(30) Foreign Application Priority Data

Jan. 16, 2014 (DE) .................. 10 2014 100 444

(51) Int. Cl.
*A61G 13/06* (2006.01)
*A61G 13/02* (2006.01)
(Continued)

(52) U.S. Cl.
CPC .............. *A61G 13/06* (2013.01); *A61G 13/02* (2013.01); *F16H 19/04* (2013.01); *A61B 5/704* (2013.01)

(58) Field of Classification Search
CPC ........ A61G 13/06; A61G 13/02; F16H 19/04; A61B 5/704; A63B 21/0083; A63B 21/0087
See application file for complete search history.

(56) References Cited

U.S. PATENT DOCUMENTS 3,722,365 A * 3/1973 Olsson ..................... B23H 7/18
 91/1
3,765,251 A * 10/1973 Whitenack, Jr. ........ B66F 9/141
 74/29
(Continued)

FOREIGN PATENT DOCUMENTS

CN 1446065 A 10/2003
CN 101991430 A 3/2011
(Continued)

OTHER PUBLICATIONS

International Search Report dated May 4, 2015 issued for corresponding international application No. PCT/EP2015-050659, 2 pages.
(Continued)

*Primary Examiner* — David R Hare
*Assistant Examiner* — Alexis Felix Lopez

(57) ABSTRACT

An apparatus is disclosed. The apparatus includes an operating table column head assembly, a patient support surface assembly that is movable relative to the operating table column head assembly, and an actuating cylinder configured to move the patient support surface assembly relative to the operating table column head assembly, the actuating cylinder including a piston rod. A first gear rack is attached to the operating table column head assembly and a second gear rack is attached to the patient support surface assembly. A gear assembly is disposed on the piston rod of the actuating cylinder. The gear assembly engages with the first gear rack and the second gear rack. The first gear rack and the second gear rack move in substantially opposite directions relative to the gear assembly, when the actuating cylinder is actuated.

18 Claims, 3 Drawing Sheets

(51) Int. Cl.
*F16H 19/04* (2006.01)
*A61B 5/00* (2006.01)

(56) References Cited

U.S. PATENT DOCUMENTS

| | | | | |
|---|---|---|---|---|
| 3,982,741 | A * | 9/1976 | Mitchell | A61G 7/015 5/614 |
| 4,501,414 | A * | 2/1985 | Mason | A61G 13/02 378/209 |
| 5,272,776 | A * | 12/1993 | Kitamura | A61B 5/0555 5/600 |
| 5,275,064 | A * | 1/1994 | Hobbs | F16H 19/04 108/143 |
| 5,279,011 | A * | 1/1994 | Schnelle | A61G 13/08 5/616 |
| 5,326,247 | A * | 7/1994 | Prenzel | B21C 23/211 425/185 |
| 6,505,365 | B1 * | 1/2003 | Hanson | A61G 7/005 5/510 |
| 6,507,964 | B1 * | 1/2003 | Lewandowski | A61G 7/012 5/600 |
| 6,581,910 | B1 * | 6/2003 | Granata | B66F 7/02 254/105 |
| 6,615,428 | B1 * | 9/2003 | Pattee | A61B 6/04 108/143 |
| 7,028,356 | B2 * | 4/2006 | Somasundaram | A61B 6/105 5/600 |
| 7,430,772 | B2 * | 10/2008 | Van Es | A61B 5/0555 378/209 |
| 2002/0029419 | A1 * | 3/2002 | Weil | A61B 6/0457 5/601 |
| 2003/0001346 | A1 | 1/2003 | Hamilton | B60G 17/0152 280/5.515 |
| 2004/0098804 | A1 * | 5/2004 | Varadharajulu | A61B 6/0457 5/611 |
| 2006/0042009 | A1 * | 3/2006 | Somasundaram | A61B 6/0457 5/601 |
| 2006/0280580 | A1 * | 12/2006 | Lutz | B65G 1/0492 414/222.03 |
| 2007/0221054 | A1 * | 9/2007 | Webster | F15B 15/1409 91/394 |
| 2008/0045831 | A1 * | 2/2008 | Cho | A61B 5/0555 600/415 |
| 2009/0000409 | A1 * | 1/2009 | Hammerer | B23Q 5/385 74/89.17 |
| 2009/0031833 | A1 * | 2/2009 | Wada | B41J 19/00 74/22 R |
| 2009/0320206 | A1 * | 12/2009 | Dyreby | A47B 9/20 5/611 |
| 2010/0293713 | A1 * | 11/2010 | Sharps | A61G 7/001 5/86.1 |
| 2011/0083273 | A1 * | 4/2011 | Sharps | A61G 13/02 5/624 |
| 2011/0239795 | A1 * | 10/2011 | Uchida | F16H 19/04 74/89.17 |
| 2011/0271779 | A1 * | 11/2011 | Corcoran | F16H 25/20 74/89.23 |
| 2011/0296613 | A1 * | 12/2011 | Farmbauer | A61B 5/0555 5/600 |
| 2012/0010542 | A1 * | 1/2012 | Yu | A61G 13/02 601/2 |
| 2013/0219621 | A1 * | 8/2013 | Eder | A61B 6/0407 5/601 |
| 2013/0251113 | A1 * | 9/2013 | Taku | A61B 5/0091 378/208 |
| 2013/0255531 | A1 * | 10/2013 | Culver | B62D 3/12 105/157.1 |
| 2013/0287597 | A1 * | 10/2013 | McNichol | F04B 47/08 417/53 |
| 2013/0312188 | A1 * | 11/2013 | Jackson | A61G 7/015 5/618 |
| 2014/0026692 | A1 * | 1/2014 | Lim | F16H 19/04 74/29 |
| 2014/0083436 | A1 * | 3/2014 | Pettinato | A61B 6/0428 128/870 |
| 2014/0208894 | A1 * | 7/2014 | Miller | F16H 19/04 74/665 G |
| 2014/0215718 | A1 * | 8/2014 | Wootton | A61G 13/0036 5/621 |
| 2014/0354132 | A1 * | 12/2014 | Jessie | F25D 25/025 312/334.8 |
| 2015/0000433 | A1 * | 1/2015 | Farcy | F16H 19/04 74/30 |
| 2015/0045676 | A1 * | 2/2015 | Dawson | A61G 13/121 600/476 |
| 2015/0144063 | A1 * | 5/2015 | Braun | F16H 57/02004 118/726 |
| 2015/0289665 | A1 * | 10/2015 | Klimm | F16H 19/04 74/89.14 |
| 2015/0290690 | A1 * | 10/2015 | Claasen | B21C 23/211 72/273 |
| 2015/0291205 | A1 * | 10/2015 | Nishitani | B62D 3/123 74/409 |
| 2015/0308527 | A1 * | 10/2015 | Nagel | B60T 13/746 74/89.14 |
| 2016/0270994 | A1 * | 9/2016 | Staudinger | F16H 19/04 |
| 2017/0107779 | A1 * | 4/2017 | Akhare | E21B 33/063 |
| 2017/0211340 | A1 * | 7/2017 | Alford | E21B 19/07 |

FOREIGN PATENT DOCUMENTS

| | | |
|---|---|---|
| CN | 201768121 U | 3/2011 |
| CN | 202802057 U | 3/2013 |
| DE | 3621480 A1 | 1/1988 |
| DE | 10196489 T1 | 7/2003 |
| DE | 60019130 T2 | 9/2005 |
| DE | 102009038785 A1 | 3/2011 |
| JP | 06-042601 A | 2/1994 |
| JP | 2003-505201 A | 2/2003 |
| JP | 2003-339798 A | 12/2003 |
| TW | 454511 U | 9/2001 |
| WO | 01/08621 A2 | 2/2001 |
| WO | 02/098342 A1 | 12/2002 |
| WO | 2009/047279 A2 | 4/2009 |

OTHER PUBLICATIONS

Japanese Office Action (with English translation) dated Oct. 30, 2018 during the prosecution of corresponding Japanese Patent Application No. 2016-7546757, 16 pages.
Korean Office Action dated Jun. 28, 2018 during the prosecution of corresponding Korean Patent Application No. 10-2016-7022108, 3 pages.
Russian Search Report dated Jul. 16, 2018 during the prosecution of corresponding Russian Patent Application No. 2016133377, 2 pages.
Office Action and Search Report dated May 4, 2017 issued for corresponding Chinese application No. CN201580003418.0, 22 pages.

* cited by examiner

DEVICE FOR LINEARLY MOVING A PATIENT SUPPORT SURFACE USING A HYDRAULIC CYLINDER AND A GEAR ARRANGEMENT

CROSS REFERENCE TO RELATED APPLICATIONS

The present application is a continuation-in-part filed under 35 U.S.C. § 111(a), and claims the benefit under 35 U.S.C. §§ 365(c) and 371 of PCT International Application No. PCT/EP2015/050659, filed Jan. 15, 2015, and which designates the United States of America, and German Patent Application No. 10 2014 100 444.2, filed Jan. 16, 2014. The disclosures of these applications are herein incorporated by reference in their entirety.

TECHNICAL FIELD

The disclosure relates to a device for linearly moving a patient support unit, said device comprising a stationary column head unit and a support surface unit which can be moved relative to the column head unit in a linear manner, and on which the patient support surface can be secured. The device may further comprise a hydraulic cylinder for moving the support surface unit relative to the column head unit.

BACKGROUND

Standard operating tables typically consist of an operating table base, a height-adjustable column and a patient support surface on which the patient is placed for an operation. To allow the patient to be x-rayed during surgery, the patient support surface may be movable relative to the column in such a way as to create a radiotransparent area in which, for example, a C-arm of an x-ray device can be guided.

There are several known methods for moving the support surface unit, on which the patient support surface can be attached, relative to the stationary column head unit, which is disposed on the side of the operating table that faces away from the operating table base. For one, operating tables are known in which the support surface unit can be moved manually relative to the stationary column head unit. This has the disadvantage that manually corresponding forces are applied for this purpose, and thus operating convenience is diminished. In addition, it may be difficult to implement a relatively precise targeted method. To avoid these disadvantages, the support surface unit may be moved relative to the column head unit by an electric motor.

The support surface unit may also be moved relative to the column head unit hydraulically with the aid of one or more hydraulic cylinders. The problem with such hydraulic solutions is that the cylinder is longer than the stroke it can execute. This results in a relatively long structural length, which generally is not available in the column head of the operating table, so that movement by a simple hydraulic cylinder can be difficult.

It is further known to use two hydraulic cylinders for moving the support surface unit relative to the column head unit, with these hydraulic cylinders being arranged adjacent to one another such that when one cylinder is actuated the other cylinder is moved along, so that their strokes together total the required total stroke. The problem with this solution, however, is that it is relatively expensive and involves a relatively large installation space widthwise.

SUMMARY OF THE DISCLOSURE

A device for linearly moving a patient support surface with the aid of a hydraulic cylinder and a method for assembling said device, which allow for a simple compact structure, are disclosed.

In at least some exemplary embodiments, at least one first gear rack may be attached to the column head unit and at least one second gear rack may be attached to the support surface unit. A gear assembly may be provided on the piston rod of the hydraulic cylinder, for example at the end of the piston rod that faces away from the cylinder tube, said gear assembly engaging with the first gear rack in such a way that the gear assembly rolls on both the first gear rack and the second gear rack when the hydraulic cylinder is actuated. The gear assembly may for example roll on the first and second gear racks in opposite directions.

Regarding this rolling of the gear assembly on the gear racks arranged on the two units, the entire travel path along which the support surface unit is moved relative to the column head unit may result from the total of the rolling paths of the gear assembly on the first and second gear racks. This may allow the patient support surface to be moved relative to the column head unit by a distance that is significantly greater than the stroke of the hydraulic cylinder, and therefore a hydraulic cylinder having a relatively small and/or compact configuration can be used to realize the required long adjustment path.

The rolling of the gear assembly may include, for example, one or more gear wheels of the gear assembly meshing with the gear rack and rotating accordingly as a result of the engagement.

In at least some exemplary embodiments, the gear assembly may comprise (e.g., precisely one) a single gear wheel, which meshes with both the first and the second gear rack. In this case, the total travel path along which the support surface unit can be moved relative to the column head unit may correspond to (e.g., precisely) twice the stroke of the hydraulic cylinder (or for example about twice the stroke of the hydraulic cylinder), because the gear wheel has substantially the same rolling path on the two gear racks (e.g., the rolling path that corresponds to the length of the stroke of the hydraulic cylinder). For example, a hydraulic cylinder may be used, the stroke of which may be selected such that a total travel path of between about 200 mm and about 500 mm results.

In an alternative embodiment, the gear assembly can also comprise a first and at least one second gear wheel, wherein the first gear wheel meshes with the first gear rack and the second gear wheel meshes with the second gear rack. The ratio of the sizes of the two gear wheels to one another can for example be used to adjust the gear ratio between the stroke of the hydraulic cylinder and the total travel path, so that in order to achieve the same total travel path, a relatively more compact hydraulic cylinder having a relatively shorter stroke can be used. In particular, the second gear wheel has a larger diameter than the first gear wheel.

In at least some exemplary embodiments, the tooth ratio of the first gear wheel to the second gear wheel may be between about 1:1 and about 1:4, such as for example about 12/21 or about 12/24. This may result in a gear ratio (e.g., a travel ratio) of about 1 to 2 to about 1 to 5. A tooth ratio of about 12/21 may result in a gear ratio of about 1 to 2.75. For example, in order to achieve a total travel path of about 300 mm, a single hydraulic cylinder having a stroke of about 109 mm may be used. Thus a relatively compact configuration may be achieved.

In at least some exemplary embodiments, a third gear rack may be disposed on the column head unit and the gear assembly may comprise a third gear wheel that meshes with the third gear rack. The third gear rack may be disposed for example at a predetermined distance from and parallel to the second gear rack. The first and third gear wheels may for example be the same size. Accordingly, a relatively stable configuration may be achieved, because the gear assembly can be supported on two gear racks of the column head unit. For example, the second gear wheel, which meshes with the second gear rack, may be disposed between the first and the third gear wheel.

The first, second and/or third gear wheels may be mounted for example on a common shaft in a rotationally fixed manner, and this shaft may be mounted on the piston rod so as to rotate relative thereto. This may result in a gear stack comprising the three gear wheels, which may not rotate relative to one another. If for example a single gear wheel is provided, it can optionally be likewise mounted in a rotationally fixed manner on a rotatable shaft, or can alternatively be mounted rotatably on a fixed shaft.

The shaft may be mounted rotatably on a fork head, which may be disposed at the end of the piston rod that faces away from the cylinder tube of the hydraulic cylinder. In this manner, a simple connection between the gear assembly and the piston rod may be achieved, which is suitably stable.

The column head unit may for example comprise a fastening assembly for fastening the column head unit onto a column of an operating table that can be mounted on the floor.

The support surface unit may comprise a support surface for supporting the patient support surface, on which the patient support surface may for example be fastened. The support surface unit may further have, for example, at least one cross-member disposed laterally on the support surface, on which the second toothed rack may be arranged. A further cross-member may be disposed on the opposite side of the support surface. The second gear rack may be preferably disposed on the inner side of the cross-member, that is to say the side that may face toward the column of an operating table. For example, the assembly comprising the gear racks and the hydraulic cylinder may be mounted under a covering, which may reduce the likelihood of unsuitable operation due to outside ambient conditions.

In at least some exemplary embodiments, the column head unit and the support surface unit may be connected to one another via at least one linear guide unit, for example via at least two linear guide units arranged on opposite sides, wherein the linear guide units may allow linear movement of the column head units relative to one another along a predetermined axis, and may prevent movement in a direction other than the direction defined by said predetermined axis. The linear guide units may for example each comprise a linear guide carriage, arranged on the column head unit, wherein the linear guide carriages may have longitudinal recesses aligned in the direction of the predetermined axis, with these recesses being guided on tracks provided on the support surface unit. A secure simple structure for guiding the movement may thereby be achieved, and reliable mounting may be provided.

In at least some exemplary embodiments, the hydraulic cylinder may be attached to the column head unit. For example, when the support surface unit is moved relative to the column head unit, the hydraulic cylinder may not be moved along with it. For example, part of the cylinder base may be accommodated in a recess of a frame of the column head unit, whereby a relatively simple mounting may be achieved. Alternatively, the hydraulic cylinder can also be fastened on the support surface unit.

The hydraulic cylinder may comprise a cylinder tube, a cylinder base, a piston that is movable within the cylinder and a piston rod attached to the piston. The gear assembly may be disposed at the end of the piston rod that is opposite the piston. A relatively simple configuration of the hydraulic cylinder may thereby be achieved. Accordingly, a relatively expensive, specially-designed cylinder may not be provided.

In at least some exemplary embodiments, a hydraulic cylinder may be mounted by (e.g., first) inserting a cylinder base into a cylinder tube until it is (e.g., fully) held inside the latter. A piston, a piston rod and sealing elements may then be inserted into the cylinder tube. The unit thus obtained may comprise the cylinder base, the cylinder tube, the piston, the piston rod and the sealing elements, and may be placed into receiving elements of a frame of the column head unit. The head end of the cylinder tube, from which the piston rod may project, may then be acted on by a pressure which may force a part of the cylinder base out of the cylinder tube and into a receiving bore of the frame. Finally, the oil line can be attached to the bottom side of the hydraulic cylinder. The gear assembly may be fastened at the end of the piston rod that faces away from the cylinder tube.

In at least some exemplary embodiments, providing one cylinder having a straight stroke may provide a relatively simple cylinder assembly having a relatively small number of components (e.g., in which a simple standard tube can be used as the cylinder tube). Accordingly, in at least some exemplary embodiments, a relatively simple assembly and a relatively simple design may be provided. For example, relatively costly special configurations and special sizes of the hydraulic cylinder may not be involved. Furthermore, relatively expensive screw connections, flange connections and weld seams may not be provided.

BRIEF DESCRIPTION OF THE DRAWINGS

Further features and advantages are explained in greater detail in the context of embodiment examples, in reference to the accompanying figures. The drawings show.

DETAILED DESCRIPTION AND INDUSTRIAL APPLICABILITY

Figure 1:
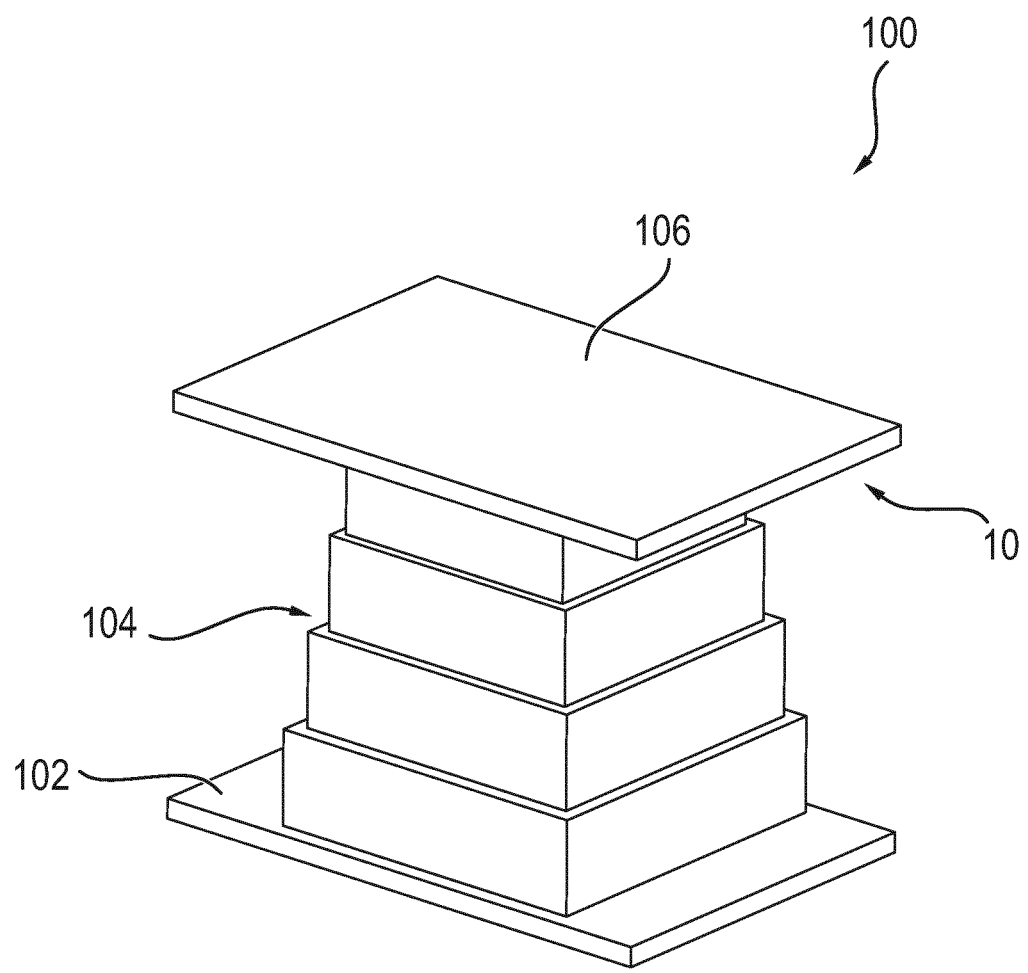
FIG. 1, a schematic, perspective representation of an operating table, according to exemplary embodiments of the present disclosure.

FIG. 1 shows a schematic, perspective, simplified representation of an operating table 100. The operating table may comprise an operating table base 102, on top of which operating table 100 can be mounted on the floor (e.g., floor-mounted). Operating table 100 may further comprise a column 104, which may be height-adjustable. On the side of column 104 that faces away from operating table base 102, a patient support surface 106 may be arranged, on which the patient can be placed.

Patient support surface 106 may be connected to column 104 by a device 10 for linearly moving the patient support surface (e.g., moving the patient support surface horizontally), so that patient support surface 106 can be moved linearly relative to column 104 in a predetermined direction along a predetermined axis. This movement may provide a suitably large radiotransparent area, within which a patient lying on patient support surface 106 can be x-rayed during an operation.

Figure 2:
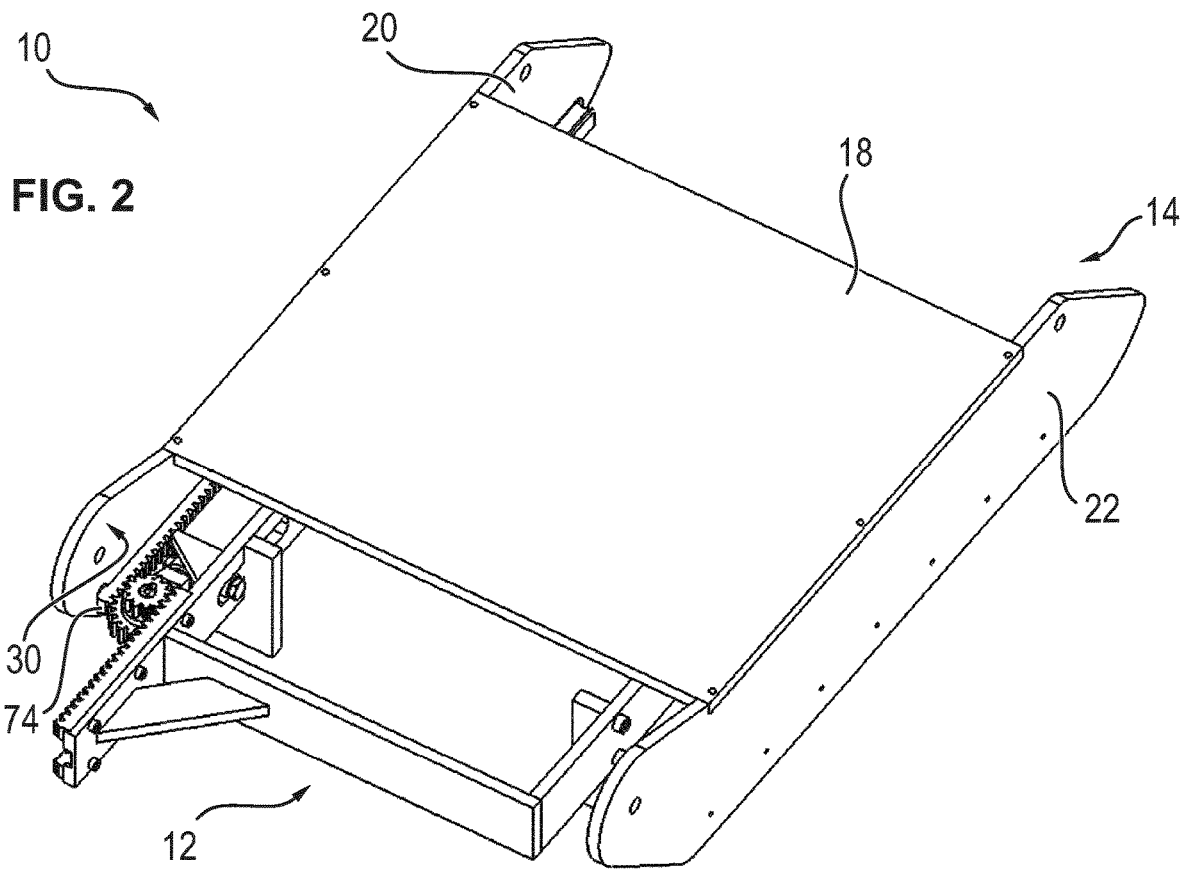
FIG. 2, a schematic, perspective representation of an exemplary device for linearly moving a patient support surface of the operating table according to FIG. 1.
Figure 3:
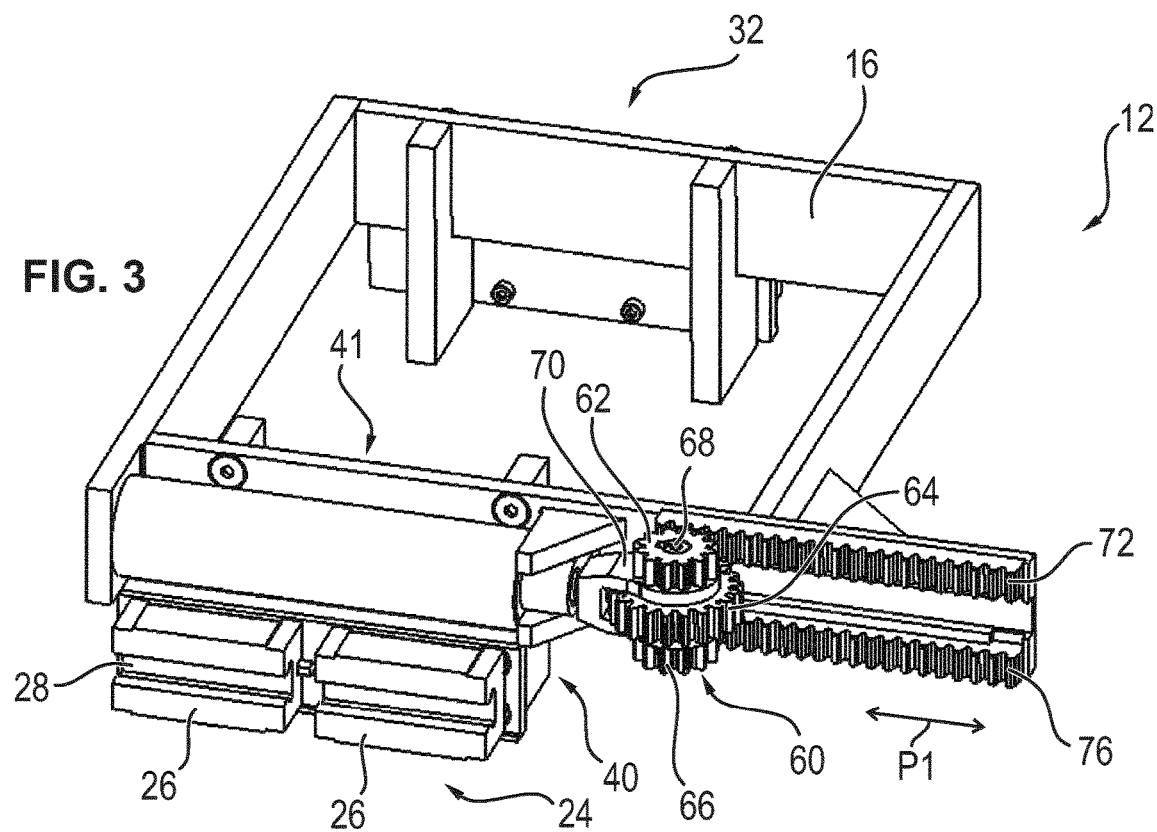
FIG. 3, a schematic, perspective representation of an exemplary column head unit of the device according to FIG. 2.
Figure 4:
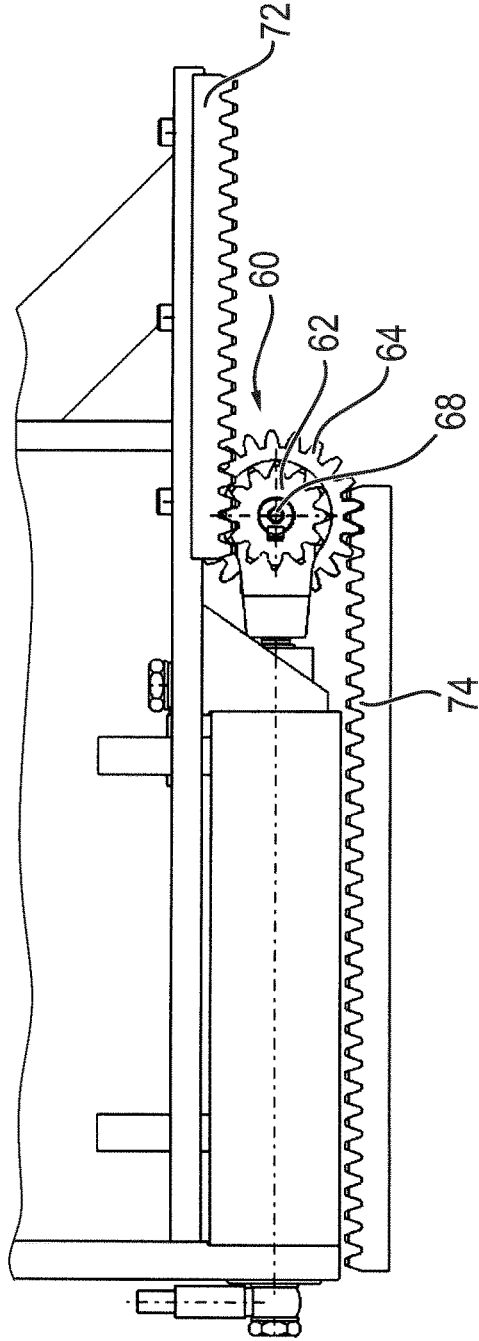
FIG. 4, a plan view of a section of the device in a first exemplary operating state.
Figure 5:
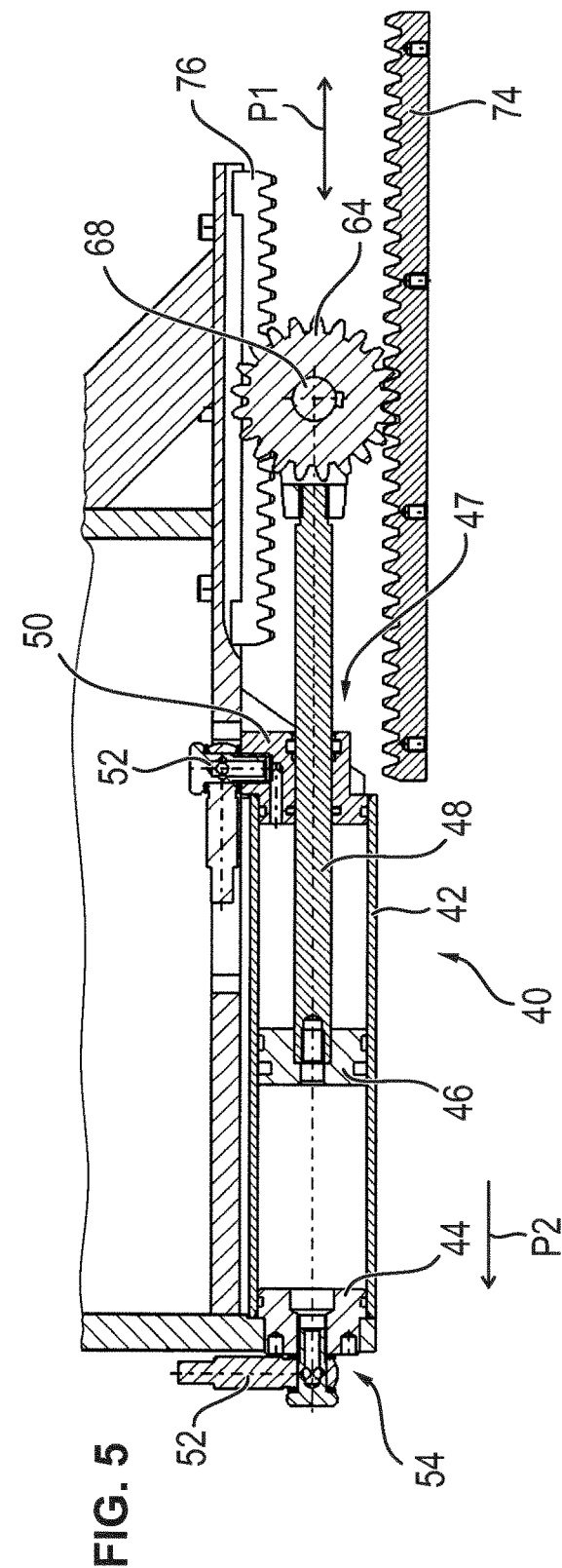
FIG. 5, a sectional representation of a section of the device according to FIGS. 2 and 4 in a second exemplary operating state.

FIG. 2 shows a schematic, perspective representation of device 10 for linearly moving (e.g., moving in a substantially horizontal direction) patient support surface 106 relative to column 104. FIG. 3 shows a schematic, perspective representation of an operating table column head assembly (e.g., column head unit 12) of device 10, and FIGS. 4 and 5 show sectional views of the device according to FIG. 2 in two different exemplary operating states, in which a patient support surface assembly (e.g., patient support unit 14) of device 10 is for example shown moved to different positions relative to column head unit 12.

Device 10 may comprise a column head unit 12, via which device 10 can be attached to column 104 of operating table 100. For example, column head unit 12 may have a frame 16, by which said attachment is provided and which may provide column head unit 12 with suitable stability.

Device 10 may have a patient support surface assembly (e.g., patient support unit 14), which may comprise a support surface 18 and two lateral cross-members 20, 22. Patient support unit 106 can be fastened onto support surface 18, by which it may be supported. Thus when support surface unit 14 is moved relative to column head unit 12, patient support surface 106 may be correspondingly moved relative to column 104.

Column head unit 12 and patient support surface 14 may be connected to one another such that they are movable relative to one another in the direction of double arrow P1 via a linear guide unit 24. This linear guide unit 24 may comprise two guide carriages 26, each having a longitudinal recess 28 extending in the direction of double arrow P1, via which the carriages may be guided on a rail, which may be disposed on the inner side 30 of cross-member 20.

For example, a second linear guide unit 32 may be disposed on the side of column head unit 12 that is opposite the first linear guide unit 24, so that support surface unit 14 and column head unit 12 may be connected to one another stably on both sides. Support surface unit 14 may be mounted on column head unit 12 by linear guide unit 24, 32 in such a way that the support surface unit may be movable linearly in the direction predetermined by linear guide unit 24, 32 while remaining securely mounted in substantially all directions other than for example the direction indicated by double arrow P1.

To implement the movement of support surface unit 14 relative to column head unit 12, an actuating cylinder (e.g., a hydraulic cylinder 40 or any other suitable type of actuating cylinder such as a pneumatic cylinder or electrically-powered cylindered) may be provided, which may be arranged in a seat 41 on frame 16. As illustrated in FIG. 5, hydraulic cylinder 40 may comprise a cylinder tube 42, a cylinder base 44 and a piston 46, which may be movably guided inside cylinder tube 42 in the direction of double arrow P1. On piston 46, a piston rod 48 may be arranged, which projects out of cylinder tube 42 on the side of hydraulic cylinder 40 that faces away from cylinder base 44.

Head end 47 of cylinder 40 may be sealed off by a cylinder head 50, in which piston rod 48 may be guided. Hydraulic connections for supplying and discharging oil for the purpose of moving piston 46 relative to cylinder tube 42 may be provided in both cylinder base 44 and cylinder head 50.

The above-described design may allow for cylinder 40 to be assembled in a relatively simple manner using standard parts, without involving relatively complex specially-manufactured parts. For mounting, cylinder base 40 may be inserted into cylinder tube 42. A relatively simple standard tube may be used as cylinder tube 42. Piston 46 and piston rod 48 together with the appropriate seals may then be inserted into cylinder tube 42. Cylinder head 50 may also be attached. Pressure may then be applied to head end 47 of hydraulic cylinder 40, which may force the cylinder base in the direction of arrow P2 and cause a part of cylinder base 44 to be received in a recess 54 of frame 16 (e.g., so that cylinder 40 may be fixed on frame 16). Hydraulic connections 52 may then be attached.

On the side of piston 48 that faces away from piston 46, a gear assembly 60 may be provided, which may comprise a first gear wheel 62, a second gear wheel 64 and a third gear wheel 66, which may be mounted in a rotationally fixed manner on a common shaft 68 (e.g., forming a gear stack). For example, first gear wheel 62, second gear wheel 64, and third gear wheel 66 may be mounted in a rotationally fixed manner on common shaft 68 so that first gear wheel 62, second gear wheel 64, third gear wheel 66, and common shaft 68 rotate together (e.g., rotate together as a single gear stack).

Shaft 68 may be mounted on a fork head 70, which may be fixedly attached to piston 48, such that the shaft is rotatable relative to the fork head. Gear wheels 62, 64, and 66 may rotate uniformly with shaft 68.

As illustrated in FIG. 3, a first gear rack 72 and a third gear rack 76 may be disposed on column head unit 12, which may extend parallel to one another and may be spaced from one another by a predetermined distance. On the inner side 30 of cross-member 20 of patient support surface unit 14, a second gear rack 74 may be arranged, for example extending parallel to the first and third gear racks 72, 76.

First gear wheel 62 may mesh with first gear rack 72, second gear wheel 64 may mesh with second gear rack 74, and third gear wheel 66 may mesh with third gear rack 76.

FIG. 4 shows the operating state in which piston rod 48 is pushed into cylinder tube 42 (e.g., pushed all the way into cylinder tube 42). When hydraulic cylinder 40 is actuated, piston rod 48 may be moved out of cylinder tube 42, thereby moving support surface unit 14 relative to column head unit 12.

This movement may cause the first and third gear wheels 62, 66 to roll along the first and third gear racks 72, 76 in the opposite direction from the second gear wheel 64 rolling along the second gear rack 74. For example, as illustrated in FIGS. 4 and 5, gear wheels 62, 64, and 66 and shaft 68 may all rotate together, with teeth of first gear wheel 62 and third gear wheel 66 meshing with teeth of first gear rack 72 and third gear rack 76, respectively, and teeth of second gear wheel 64 meshing with teeth of second gear rack 74. As gear wheels 62, 64, and 66 and shaft 68 rotate together, first gear rack 72 and third gear rack 76 may move in a first direction relative to gear assembly 60 that is substantially opposite to a second direction in which second gear rack 74 moves relative to gear assembly 60. Further for example, gear assembly 60 may engage with first gear rack 72 and second gear rack 74, wherein first gear rack 72 and second gear rack 74 may move (e.g., may be moved) in substantially opposite directions, relative to gear assembly 60, when the actuating cylinder (e.g., hydraulic, pneumatic, or electrically-powered cylinder 40) is actuated. This may provide the rolling paths to be added together to form the travel path along which support surface unit 14 is moved relative to column head unit 12. This exemplary configuration may allow for a relatively large total travel path to be provided by a relatively short stroke, allowing for a relatively small, compact hydraulic cylinder 40 of relatively simple design, which can be relatively easily integrated into frame structure 16 of column head 12.

In at least some exemplary embodiments, the tooth ratio of first gear wheel 62 to second gear wheel 64, and also the tooth ratio of third gear wheel 66 to second gear wheel 64, may be 12/21. This tooth ratio may provide a gear ratio between the stroke and the total achieved travel path of about 1 to about 2.75. For example, the total travel path may be between about 200 mm and about 500 mm.

In at least some exemplary embodiments, additional tooth ratios may also be selected, resulting in varying gear ratios, thereby providing for the ratio between the length of hydraulic cylinder 40 and the total achievable travel path to be adjusted. For example, different tooth ratios may be pre-selected to produce desired gear ratios.

In at least some exemplary embodiments, third gear rack 76 and also third gear wheel 66 may not be provided.

In at least some exemplary embodiments, hydraulic cylinder 40 may be attached to support surface unit 14.

In at least some exemplary embodiments, a single gear wheel (e.g., only one gear wheel 62 to 66) may be provided, which may mesh into two rails 72, 74, one of which may be disposed on column head unit 12 and the other of which may be disposed on support surface unit 14. For example, the gear ratio may be about 1 to about 2, and therefore the total movement path may correspond to about twice the stroke of cylinder 40. This exemplary arrangement may allow for a relatively simple and cost-effective configuration.

It will be apparent to those skilled in the art that various modifications and variations can be made to the disclosed method and apparatus. Other embodiments will be apparent to those skilled in the art from consideration of the specification and practice of the disclosed method and apparatus. It is intended that the specification and the disclosed examples be considered as exemplary only, with a true scope being indicated by the following claims.

What is claimed is:

1. An apparatus, comprising:
an operating table column head assembly;
a patient support surface assembly that is movable relative to the operating table column head assembly, the patient support surface assembly comprising:
a support surface having a length; and
at least one lateral cross-member disposed along at least a portion of the length of the support surface; and
an actuating cylinder configured to move the patient support surface assembly relative to the operating table column head assembly, the actuating cylinder including a piston rod;
wherein a first gear rack is attached to the operating table column head assembly;
wherein a second gear rack is attached to the at least one lateral cross-member;
wherein a gear assembly is disposed on the piston rod of the actuating cylinder, the gear assembly comprising a first gear wheel and a second gear wheel which rotate together;
wherein the second gear wheel has a diameter that is larger than a diameter of the first gear wheel;
wherein the first gear wheel is disposed to engage with the first gear rack, and the second gear wheel is disposed to engage with the second gear rack to drive movement of the second gear rack;
wherein the first gear rack and the second gear rack move in substantially opposite directions relative to the gear assembly when the actuating cylinder is actuated; and
wherein when the actuating cylinder is actuated, it causes movement of the patient surface assembly relative to the operating table column assembly by a distance greater than double a stroke distance of the actuating cylinder.

2. The apparatus of claim 1, wherein the actuating cylinder is a hydraulic cylinder.

3. The apparatus of claim 1, wherein the first gear wheel and the second gear wheel are both rotationally fixed on a common shaft.

4. The apparatus of claim 1, wherein the operating table head assembly is connected to a column of an operating table.

5. The apparatus of claim 3, wherein a tooth ratio of the first gear wheel to the second gear wheel is between about 1 to 1 and about 1 to 4.

6. The apparatus of claim 3, wherein:
a third gear rack is disposed on the operating table column head assembly, the third gear rack extending parallel to and being spaced a predetermined distance from the first gear rack; and
the gear assembly includes a third gear wheel that meshes with the third gear rack.

7. The apparatus of claim 3, wherein:
the first gear wheel, the second gear wheel, and a third gear wheel share a common shaft and are rotationally fixed with respect to each other; and
the shaft is mounted on the piston rod so as to be rotatable relative to the piston rod.

8. The apparatus of claim 7, wherein the shaft is mounted rotatably on a fork head that is disposed at an end of the piston rod that faces away from a cylinder tube of the actuating cylinder.

9. An apparatus, comprising:
an operating table column head assembly;
a patient support surface assembly that is movable relative to the operating table column head assembly; and
a hydraulic cylinder configured to move the patient support surface assembly relative to the operating table column head assembly, the hydraulic cylinder including a piston rod;
wherein a first gear rack is attached to the operating table column head assembly;
wherein a second gear rack is attached to the patient support surface assembly;
wherein a gear assembly is disposed on the piston rod of the hydraulic cylinder, the gear assembly including a first gear wheel and a second gear wheel, wherein the first gear wheel and the second gear wheel have different diameters;
wherein the first gear wheel is disposed to engage with the first gear rack and the second gear wheel is disposed to engage with the second gear rack;
wherein the first gear rack moves in a first direction relative to the gear assembly, and the second gear rack moves in a second direction relative to the gear assembly, when the hydraulic cylinder is actuated, and wherein the patient support surface assembly includes at least one cross-member, the second gear rack being attached to an inner side of the at least one cross-member.

10. The apparatus of claim 9, wherein the first direction is substantially opposite to the second direction.

11. The apparatus of claim 9, wherein the operating table column head assembly includes a fastening assembly that fastens the operating table column head assembly onto a column that is floor-mounted.

12. The apparatus of claim 9, wherein the operating table column head assembly and the patient support surface assembly are connected to one another via two linear guide units disposed on opposite sides of the operating table column head assembly.

13. The apparatus of claim 12, wherein the linear guide units allow linear movement of the operating table column head assembly and the patient support surface assembly relative to one another along a predetermined axis.

14. The apparatus of claim 9, wherein a cylinder tube or a cylinder base of the hydraulic cylinder is fastened onto the operating table column head assembly.

15. The apparatus of claim 9, wherein:
the hydraulic cylinder includes a cylinder tube, a cylinder base, and a piston that is movable inside the cylinder tube;
the piston is attached to a first end of the piston rod; and
the gear assembly is disposed at a second end of the piston rod.

16. An apparatus, comprising:
an operating table column head assembly having a frame defining a longitudinal axis;
a patient support surface assembly that is movable relative to the operating table column head assembly and along the longitudinal axis, the patient support surface assembly comprising:
a support surface having a length; and
at least one lateral cross-member disposed along at least a portion of the length of the support surface; and a hydraulic cylinder configured to move the patient support surface assembly relative to the operating table column head assembly along the longitudinal axis, the hydraulic cylinder attached to a lateral surface of the frame and oriented along a length of the operating table column head assembly, the hydraulic cylinder including a piston rod;
wherein a first gear rack is attached to the operating table column head assembly;
wherein a second gear rack is attached to the at least one lateral cross-member;
wherein a third gear rack is attached to the operating table column head assembly;
wherein a gear assembly is disposed on the piston rod of the hydraulic cylinder, the gear assembly including a first gear wheel, a second gear wheel, and a third gear wheel;
wherein the first gear wheel is disposed to engage with the first gear rack, the second gear wheel is disposed to engage with the second gear rack, and the third gear wheel is disposed to engage with the third gear rack; and
wherein the first gear rack moves in a first direction relative to the gear assembly, the second gear rack moves in a second direction relative to the gear assembly, and the third gear rack moves in the first direction relative to the gear assembly, when the hydraulic cylinder is actuated.

17. The apparatus of claim 16, wherein the first direction is substantially opposite to the second direction.

18. The apparatus of claim 16, wherein:
the hydraulic cylinder comprises a cylinder base received substantially within a cylinder tube;
a piston, the piston rod, and a plurality of sealing elements are inserted into the cylinder tube;
an oil line is attached to a base side of the hydraulic cylinder; and
the gear assembly is attached to the end of the piston rod that faces away from the cylinder tube.

* * * * *